United States Patent
Morisaki et al.

(10) Patent No.: US 12,357,544 B2
(45) Date of Patent: Jul. 15, 2025

(54) CURABLE COMPOSITION FOR DENTISTRY

(71) Applicant: TOKUYAMA DENTAL CORPORATION, Tokyo (JP)

(72) Inventors: Hiroshi Morisaki, Tokyo (JP); Tatsuya Yamazaki, Tokyo (JP); Takuma Matsuo, Tokyo (JP); Hironobu Akizumi, Tokyo (JP)

(73) Assignee: TOKUYAMA DENTAL CORPORATION, Tokyo (JP)

( * ) Notice: Subject to any disclaimer, the term of this patent is extended or adjusted under 35 U.S.C. 154(b) by 616 days.

(21) Appl. No.: 17/788,253

(22) PCT Filed: Nov. 26, 2020

(86) PCT No.: PCT/JP2020/043971
§ 371 (c)(1),
(2) Date: Jun. 22, 2022

(87) PCT Pub. No.: WO2021/131476
PCT Pub. Date: Jul. 1, 2021

(65) Prior Publication Data
US 2023/0039514 A1     Feb. 9, 2023

(30) Foreign Application Priority Data
Dec. 24, 2019   (JP) ................ 2019-232334

(51) Int. Cl.
| A61K 6/887 | (2020.01) |
| A61K 6/62 | (2020.01) |
| A61K 6/76 | (2020.01) |
| A61K 6/853 | (2020.01) |
| A61K 6/878 | (2020.01) |

(52) U.S. Cl.
CPC ............ *A61K 6/887* (2020.01); *A61K 6/62* (2020.01); *A61K 6/76* (2020.01); *A61K 6/853* (2020.01); *A61K 6/878* (2020.01)

(58) Field of Classification Search
CPC ........ A61K 6/887; A61K 6/853; A61K 6/878; A61K 6/76; A61K 6/62
See application file for complete search history.

(56) References Cited

U.S. PATENT DOCUMENTS

| 6,221,931 B1 | 4/2001 | Sakuma et al. |
| 8,476,338 B2 | 7/2013 | Okubayashi et al. |
| 2013/0005846 A1 | 1/2013 | Yamazaki et al. |
| 2014/0213687 A1 | 7/2014 | Yamazaki et al. |
| 2016/0136059 A1 | 5/2016 | Hecht et al. |
| 2017/0049665 A1 | 2/2017 | Kita et al. |
| 2018/0263861 A1 | 9/2018 | Bringley et al. |
| 2019/0192386 A1 | 6/2019 | Fukudome et al. |
| 2019/0292278 A1 | 9/2019 | Akizumi et al. |

FOREIGN PATENT DOCUMENTS

| EP | 3369410 A1 | 9/2018 | |
| EP | 3508190 A1 | 7/2019 | |
| JP | 2000080013 A | 3/2000 | |
| JP | 2017036224 A | 2/2017 | |
| RU | 2650632 C2 | 4/2018 | |
| WO | 2011115007 A1 | 9/2011 | |
| WO | 2013039169 A1 | 3/2013 | |
| WO | 2015125470 A1 | 8/2015 | |
| WO | WO-2018043595 A1 * | 3/2018 | ........... A61K 6/0073 |

OTHER PUBLICATIONS

WO2018043595A1 Machine translation (Year: 2018).*
International Search Report issued in corresponding International Application No. PCT/JP2020/043971; mailed Jan. 19, 2021 (2 pages).
Written Opinion of the International Searching Authority issued in corresponding International Application No. PCT/ JP2020/043971; dated Jan. 19, 2021 (3 pages).
Extended European Search Report issued in corresponding European Patent Application No. 20907449.1, dated Dec. 22, 2023 (8 pages).
Office Action issued in corresponding Russian Patent Application No. 2022118765, dated Dec. 12, 2023, with translation (15 pages).

* cited by examiner

*Primary Examiner* — Mark Eashoo
*Assistant Examiner* — Caitlin Norine Illing
(74) *Attorney, Agent, or Firm* — Osha Bergman Watanabe & Burton LLP

(57) ABSTRACT

Provided is a curable composition that is for dentistry and that contains: a polymerizable monomer (A); an inorganic filler (B) having an average particle size of 0.1-1 μm; an organic-inorganic composite filler (C) having an aggregate structure in which inorganic primary particles having an average particle size of 10-1000 nm are bonded together through a resin layer covering the surface of the particles, to form a void having a specific pore volume; and a polymerization initiator (D). In the organic-inorganic composite filler (C), a curved surface-shaped organic-inorganic composite filler (C1) formed of organic-inorganic composite aggregate particles having a curved surface shape, and an amorphous organic-inorganic composite filler (C2) formed of amorphous organic-inorganic composite aggregate particles having an edge portion, are mixed such that C1/(C1+C2) equals 0.2-0.8 in terms of the number of particles having a particle size of 5 μm or more.

5 Claims, No Drawings

CURABLE COMPOSITION FOR DENTISTRY

TECHNICAL FIELD

The present invention relates to a curable composition for dentistry, which contains an organic-inorganic composite filler.

BACKGROUND ART

The curable composition for dentistry is generally a paste-like composition containing a polymerizable monomer (monomer), a filler and a polymerization initiator as main components, and the type, shape, particle size, filling amount and the like of the filler to be used affect the operability of the curable composition for dentistry, aesthetic properties and mechanical strength of the cured body obtained by curing.

For example, when the curable composition for dentistry contains an inorganic filler having a large particle size, the mechanical strength of the cured body increases, but the surface smoothness and abrasion resistance of the cured body deteriorate, thus making it difficult to obtain the same glossy finished surface as that of natural teeth. Meanwhile, when the curable composition for dentistry contains a fine inorganic filler having an average particle size of 1 μm or less, the surface smoothness and abrasion resistance of the cured body can be improved, but the fine inorganic filler has a large specific surface area, leading to significant increase in viscosity of the curable composition for dentistry. When treating teeth, it needs to adjust consistency of the curable composition for dentistry to the consistency suited for use in the oral cavity, and when the amount of the fine inorganic filler mixed is reduced to decrease the consistency, there may occur deterioration of the operability during the treatment, increase in polymerization shrinkage rate when the curable composition for dentistry is cured, and reduction in mechanical strength of the thus obtained cured body.

In order to avoid such a trade-off relationship, the use of an organic-inorganic composite filler has been proposed (see, for example, Patent Documents 1 and 2). The organic-inorganic composite filler is a composite filler containing a fine inorganic filler in an organic resin, and the use of this filler makes it possible to maintain excellent surface smoothness and abrasion resistance when using the fine inorganic filler, and to reduce the polymerization shrinkage rate. When the amount of the organic-inorganic composite filler mixed is too large, the dryness occurs in a paste state, leading to deterioration of the operability of the paste. However, by using in combination with an inorganic filler (inorganic particles) having an average particle size of 0.1 to 1 μm, it is possible to prevent deterioration of the operability to obtain a paste-like curable composition for dentistry which is excellent in operability (see, for example, Patent Document 2).

The method for producing the organic-inorganic composite filler is commonly a method in which a curable composition obtained by kneading a fine inorganic filler and a polymerizable monomer in advance is polymerized to obtain a cured body, and then the cured body is pulverized. However, the composition including the organic-inorganic composite filler produced by this method has a problem such as low strength as the curable composition for dentistry because of weak bonding at the interface between the matrix and the organic-inorganic composite filler.

There has been proposed, as the organic-inorganic composite filler for improving this problem, an organic-inorganic composite filler having aggregation gaps in which a pore volume (volume of pores having a pore size in the range of 1 to 500 nm) measured by the mercury intrusion method is 0.01 to 0.30 $cm^3/g$ (hereinafter also referred to as "porous organic-inorganic composite filler") (see, for example, Patent Document 3). Patent Document 3 describes that a curable composition for dentistry, containing such a porous organic-inorganic composite filler, a polymerizable monomer and a polymerization initiator has satisfactory paste operability and small polymerization shrinkage rate, and also the cured body thereof has satisfactory surface smoothness and abrasion resistance, and that the porous organic-inorganic composite filler is retained in the cured body with a high fitting force by the anchor effect caused by introduction of the polymerizable monomer into the aggregation gaps due to a capillary phenomenon and curing of the polymerizable monomer, thus leading to an improvement in mechanical strength.

Patent Document 1: Japanese Unexamined Patent Application, Publication No. 2000-80013
Patent Document 2: PCT International Publication No. WO2015/125470
Patent Document 3: PCT International Publication No. WO2011/115007

DISCLOSURE OF THE INVENTION

Problems to be Solved by the Invention

The present inventors have made a study on a (paste-like) curable composition for dentistry in which a porous organic-inorganic composite filler produced according to the method disclosed in Patent Document 3 and an inorganic filler having an average particle size of 0.1 to 1 μm are used in combination. As a result, it is possible to obtain the desired effect, that is, the effect of being capable of suppressing the dryness in a paste state and affording a cured body having excellent mechanical strength, abrasion resistance and aesthetic properties, while the stickiness may occur in a paste state, leading to deterioration of the operability thus confirming that such a phenomenon is particularly remarkably observed after long-term storage, and the ability to retain the occlusal form formed when filling molars Class I cavities, etc. is slightly low. That is, it has been found that there is room for improvement in the curable composition for dentistry in which a porous organic-inorganic composite filler produced according to the method disclosed in Patent Document 3 and an inorganic filler having an average particle size of 0.1 to 1 μm are used in combination, with respect to the operability and shape retention of the paste.

Thus, it is an object of the present invention to provide a curable composition for dentistry, which affords a cured body having high mechanical strength, and has satisfactory operability and shape retention in a paste state before curing, and is also capable of maintaining satisfactory operability over a long period of time.

Means for Solving the Problems

In order to solve the above problems, the present inventors have made a study on preparation conditions of a curable composition for dentistry in which a porous organic-inorganic composite filler produced according to the method disclosed in Patent Document 3 and an inorganic filler having an average particle size of 0.1 to 1 μm are used in combination. As a result, it became clear that, when the polymerizable monomer, the inorganic filler and the porous organic-inorganic composite filler are kneaded for a long time, the operability of the paste is significantly improved, and even after long-term storage, satisfactory operability immediately after preparation may be maintained. As a result of further study based on the obtained findings, the present inventors have found that, after kneading for a long time, a part of the porous organic-inorganic composite filler which was substantially spherical at the time of mixing was pulverized into an irregular shape; the above-mentioned improvement effect can be obtained when a ratio of the amount of the porous organic-inorganic composite filler which maintains a substantially spherical shape without being pulverized and the amount of the porous organic-inorganic composite filler which was pulverized into an irregular shape is in a specific range; and the same effect can be obtained even when mixing an amorphous porous organic-inorganic composite filler pulverized separately from the beginning without being kneaded for a long time in a predetermined ratio; and thus the present invention has been completed.

Thus, the curable composition for dentistry according to the present invention contains a polymerizable monomer (A); an inorganic filler (B) having an average particle size of 0.1 to 1 µm; an organic-inorganic composite filler (C), and a polymerization initiator (D). The organic-inorganic composite filler (C) includes organic-inorganic composite aggregate particles having an aggregated structure where inorganic primary particles having an average particle size of 10 to 1,000 nm are bonded together through a resin layer covering at least part of the surface of the inorganic primary particles so as to form a void. The organic-inorganic composite filler (C) has pores, where a total pore volume of pores having a pore size measured by a nitrogen adsorption method in the range of 1 to 500 nm is 0.01 to 0.30 cm$^3$/g, and the organic-inorganic composite filler (C) has an average particle size of 10 to 100 µm. The organic-inorganic composite filler (C) includes a curved surface-shaped organic-inorganic composite filler (C1) composed of organic-inorganic composite aggregate particles having a curved surface shape, and an irregular-shaped organic-inorganic composite filler (C2) composed of organic-inorganic composite aggregate particles having an irregular shape which includes an edge portion. A content ratio {C1/(C1+C2)} of the curved surface-shaped organic-inorganic composite filler (C1) accounting for the entire organic-inorganic composite filler (C) is 0.2 to 0.8, the content ratio being expressed in terms of a ratio of the total number of the curved surface-shaped organic-inorganic composite aggregate particles which have a particle size of 5 µm or more and which constitute the curved surface-shaped organic-inorganic composite filler (C1), accounting for the total number of the organic-inorganic composite aggregate particles having a particle size of 5 µm or more.

Effects of the Invention

The curable composition for dentistry according to the present invention not only exerts the effect of affording a cured body which exhibits less polymerization shrinkage and is excellent in mechanical strength, abrasion resistance and esthetic properties, due to the use of the porous organic-inorganic composite filler, but also has excellent characteristics in that it suppresses the dryness in a paste state and is capable of maintaining excellent operability over a long period of time without causing deterioration of the operability due to the occurrence of stickiness even after long-term storage, and it also has satisfactory shape retention.

PREFERRED MODE FOR CARRYING OUT THE INVENTION

The curable composition for dentistry according to the embodiment of the present invention contains a polymerizable monomer (A); an inorganic filler (B) having an average particle size of 0.1 to 1 µm; an organic-inorganic composite filler (C), and a polymerization initiator (D). The organic-inorganic composite filler (C) includes organic-inorganic composite aggregate particles having an aggregated structure where inorganic primary particles having an average particle size of 10 to 1,000 nm are bonded together through a resin layer covering at least part of the surface of the inorganic primary particles so as to form a void. The organic-inorganic composite filler (C) has pores where a total pore volume of pores having a pore size measured by a nitrogen adsorption method in the range of 1 to 500 nm is 0.01 to 0.30 cm$^3$/g, and the organic-inorganic composite filler (C) has an average particle size of 10 to 100 µm. The organic-inorganic composite filler (C) includes a curved surface-shaped organic-inorganic composite filler (C1) composed of organic-inorganic composite aggregate particles having a curved surface shape, and an irregular-shaped organic-inorganic composite filler (C2) composed of organic-inorganic composite aggregate particles having an irregular shape which includes an edge portion. A content ratio {C1/(C1+C2)} of the curved surface-shaped organic-inorganic composite filler (C1) accounting for the entire organic-inorganic composite filler (C) is 0.2 to 0.8, the content ratio being expressed in terms of a ratio of the total number of the curved surface-shaped organic-inorganic composite aggregate particles which have a particle size of 5 µm or more and which constitute the curved surface-shaped organic-inorganic composite filler (C1), accounting for the total number of the organic-inorganic composite aggregate particles having a particle size of 5 µm or more.

The curable composition for dentistry according to the embodiment of the present invention solves the problems in a curable composition for dentistry in which an organic-inorganic composite filler (C) corresponding to the porous organic-inorganic composite filler disclosed in Patent Document 3 and an inorganic filler (B) having an average particle size of 0.1 to 1 µm are used in combination, and has greatest characteristics in that those composed of a mixture containing, as the organic-inorganic composite filler (C), two types of organic-inorganic composite aggregate particles having different shapes in a specific ratio are used.

The organic-inorganic composite filler (C) corresponds to the porous organic-inorganic composite filler disclosed in Patent Document 3. However, in the curable composition for dentistry according to the embodiment of the present invention, since the shape of the organic-inorganic composite aggregate particles constituting the organic-inorganic composite filler (C) is important, the organic-inorganic composite filler (C) is mentioned as an aggregate of the organic-inorganic composite aggregate particles. In Patent Document 3, the total pore volume of pores having a pore size in the range of 1 to 500 nm is measured by the mercury intrusion method. However, the present embodiment makes it a rule to employ the pore volume measured by the nitrogen adsorption method, which does not require the use of mercury that requires careful handling, specifically, the pore volume obtained by determining the pore size distribution by the BJH method from the isothermal adsorption curve measured by the BET method using nitrogen adsorption. This is because the total pore volume of pores having a pore size in the range of 1 to 500 nm can be measured by the nitrogen adsorption method, and it was confirmed by the study of the present inventors that pores having a pore size in the range of 1 to 500 nm have an extremely sharp pore distribution with a peak near the pore size of 50 nm, and pores having a pore size of less than 1 nm, which is difficult to measure by the mercury intrusion method, and pores having a pore size of more than 500 nm which is difficult to measure by the nitrogen adsorption method, are not substantially present.

The polymerizable monomer component (A), the inorganic filler (B) having an average particle size of 0.1 to 1 μm and the polymerization initiator (D), which are components other than the organic-inorganic composite filler (C) in the curable composition for dentistry according to the embodiment of the present invention, are not particularly different from those in a conventional curable composition for dentistry, for example, the curable compositions for dentistry mentioned in Patent Document 3 and Patent Document 2. In the following, each component in the curable composition for dentistry according to the present embodiment will be described, including these components.

As used herein, the notation "x to y" using the numerical values x and y means "x or more and y or less" unless otherwise specified. When a unit is attached only to the numerical value y in such notation, the unit shall also be applied to the numerical value x. As used herein, the term "(meth) acrylic" means both "acrylic" and "methacrylic". Similarly, the term "(meth) acrylate" means both "acrylate" and "methacrylate", and the term "(meth)acryloyl" means both "acryloyl" and "methacryloyl".

<Polymerizable Monomer (A)>

It is possible to use, as the polymerizable monomer (A), polymerizable monomers such as a radically polymerizable monomer and a cationically polymerizable monomer used in a conventional curable composition for dentistry without particular limitation. Of these, a (meth)acrylate-based polymerizable monomer, specifically, an acidic group-containing (meth)acrylate-based polymerizable monomer, a hydroxy group-containing (meth)acrylate-based polymerizable monomer, or a monofunctional or polyfunctional (meth)acrylate-based polymerizable monomer having neither an acidic group nor a hydroxy group is preferably used.

Examples of the acidic group-containing (meth)acrylate-based polymerizable monomer include (meth)acrylic acid, N-(meth)acryloyl-p-aminobenzoic acid, 2-(meth)acryloyloxybenzoic acid, 2-(meth)acryloyloxyethyl phenyl hydrogen phosphate, 2-(meth)acryloyloxyethylphosphonic acid and the like. Examples of the hydroxy group-containing (meth)acrylate-based polymerizable monomer include 2-hydroxyethyl (meth)acrylate, 3-hydroxypropyl (meth)acrylate, 4-hydroxybutyl (meth)acrylate, 6-hydroxyhexyl (meth) acrylate, 2,2-bis[(3-methacryloyloxy-2-hydroxypropyloxy) phenyl]propane, 2,2-bis[4-(4-methacryloyloxy)-3-hydroxybutoxyphenyl]propane, 2,2-bis[4-(4-methacryloyloxy)-3-hydroxybutoxyphenyl]propane, 2,2-bis[4-(4-methacryloyloxy)-3-hydroxybutoxyphenyl]propane and the like. Examples of the monofunctional or polyfunctional (meth)acrylate-based polymerizable monomer having neither an acidic group nor a hydroxy group include methyl (meth)acrylate, ethyl (meth)acrylate, triethylene glycol dimethacrylate, tetraethylene glycol dimethacrylate, neopentyl glycol dimethacrylate, 1,6-hexanediol dimethacrylate, 1,9-nonanediol dimethacrylate, 1,6-bis(methacrylethyloxycarbonylamino)trimethylhexane and the like.

A plurality of types of these (meth)acrylate-based polymerizable monomers may be used in combination as necessary. From the viewpoint of suppressing the dryness while maintaining appropriate shapeability in a paste state before curing, it is preferable to use the polyfunctional (meth) acrylate-based polymerizable monomer having neither an acidic group nor a hydroxy group after being mixed with a monofunctional (meth)acrylate-based monomer having neither an acidic group nor a hydroxy group or a hydroxy group-containing (meth)acrylate-based polymerizable monomer as necessary.

<Inorganic Filler (B)>

In the curable composition for dentistry according to the embodiment of the present invention, from the viewpoint of suppressing the dryness of the paste and improving the abrasiveness, abrasion resistance and mechanical strength of the cured body, an inorganic filler (B) having an average particle size of 0.1 to 1.0 μm is mixed. From the viewpoint of the effect, the average particle size of the inorganic filler (B) is preferably 0.15 to 0.7 μm. When the average particle size of the inorganic filler (B) becomes too small, the operability of the paste of the curable composition for dentistry before curing tends to deteriorate and the mechanical strength of the cured product tends to decrease. Meanwhile, the average particle size of the inorganic filler (B) becomes too large, it tends to be difficult to obtain the gloss of the cured product after abrasion of the curable composition for dentistry.

The material of the inorganic filler (B) is not particularly limited, and those used as an inorganic filler for a filling material of a dental restoration material can be used without particular limitation. Typical materials of the inorganic filler include metal oxides such as quartz, silica, alumina, silica-titania, silica-zirconia, lanthanum glass, barium glass and strontium glass; silicate glass, fluoroaluminosilicate glass and the like. Of these, those having a refractive index in the range of 1.4 to 1.7 are preferably used. From the viewpoint of the surface smoothness of the cured body, a spherical inorganic filler is preferably used. Furthermore, the inorganic filler (B) is preferably surface-treated with a silane coupling agent such as methyltrimethoxysilane, vinyltriethoxysilane, γ-methacryloyloxypropyltrimethoxysilane, γ-glycidoxypropyltrimethoxysilane or hexamethyldisilazane since it is possible to make the compatibility with the polymerizable monomer better, leading to an improvement in mechanical strength and water resistance. The entire average particle size of these inorganic particles may be within the above range, and a plurality of inorganic fillers having different particle size ranges, average particle sizes, refractive indexes and materials may be used in combination.

<Organic-Inorganic Composite Filler (C)>

The organic-inorganic composite filler (C) is an organic-inorganic composite filler composed of organic-inorganic composite aggregate particles having an aggregated structure where inorganic primary particles having an average particle size of 10 to 1,000 nm are bonded together through a resin layer covering at least part of the surface of the inorganic primary particles so as to form a void. In the organic-inorganic composite filler (C), a total pore volume of pores having a pore size measured by the nitrogen adsorption method in the range of 1 to 500 nm is 0.01 to 0.30 $cm^3/g$, and the organic-inorganic composite filler (C) has an average particle size of 10 to 100 μm. Here, the pore size of pores forming aggregation gaps means a median pore diameter obtained based on the pore volume distribution in pores having a pore size in the range of 1 to 500 nm measured by the nitrogen adsorption method. It is preferable to use, as the organic-inorganic composite filler (C), those in which the total pore volume of pores having a pore size in the range of 3 to 300 nm, and particularly 10 to 200 nm, measured by the nitrogen adsorption method is 0.03 to 0.20 cm$^3$/g.

As mentioned above, the organic-inorganic composite filler (C) corresponds to the porous organic-inorganic composite filler disclosed in Patent Document 3, and these organic-inorganic composite fillers also have in common that they are composed of organic-inorganic composite-aggregate particles having a structure as schematically shown in FIG. 1 of Patent Document 3. However, the organic-inorganic composite filler differs from the porous organic-inorganic composite filler specifically disclosed in Patent Document 3 in that two types of organic-inorganic composite aggregate particles having different shapes are contained in a specific ratio.

Now explaining regarding this point, in Patent Document 3, inorganic primary particles having an average particle size of 10 to 1,000 nm are treated with a silane coupling agent and then spray-dried to obtain inorganic aggregate particles, which are immersed in a solution prepared by dissolving a polymerizable monomer and a polymerization initiator in an organic solvent, followed by removal of the organic solvent and further polymerization-curing to obtain a porous organic-inorganic composite filler. At this time, the inorganic aggregate particles are usually considered to be spherical, substantially spherical, donut-shaped or so-called torus-shaped such as dimples having depressions formed on the surface of the particles, and the finally obtained porous organic-inorganic composite filler is considered to have a shape corresponding to the shape of the inorganic aggregate particles. This has been confirmed in the study by the present inventors. Therefore, although it is conceivable that a small part of the porous organic-inorganic composite filler used in Patent Document 3 is pulverized and the shape is changed during the operation process, it can be said that a large part of the organic-inorganic composite aggregate particles constituting the porous organic-inorganic composite filler is a curved surface-shaped body having a curved surface shape whose main outer surface is composed of a curved surface. The main outer surface means an outer surface when the whole is viewed as one particle without considering microstructures such as openings and interiors of pores, and the curved surface shape means a spherical, substantially spherical or torus-like shape in which the main part of the outer surface (specifically, 70% or more, preferably 80% or more, and more preferably 90% or more) is composed of a smooth curved surface.

The present inventors have prepared a plurality of paste-like curable compositions for dentistry under different kneading conditions by mixing a polymerizable monomer (A), an inorganic filler (B), an organic-inorganic composite filler (C) composed of the porous organic-inorganic composite filler produced by the method disclosed in Patent Document 3, and an initiator (D), and kneading the mixture under different conditions, and have made a study on their properties. As a result, it was confirmed that, when the kneading conditions are tightened (strong and long), the operability and shapeability of the thus obtained paste after long-term storage are improved, and that the proportion of pulverized particles in the porous organic-inorganic composite filler is significantly high in the paste kneaded under these conditions. Therefore, as shown in Examples and Comparative Examples mentioned later, it was confirmed that, when a predetermined amount of the porous organic-inorganic composite filler pulverized in advance was artificially mixed, the same effect as mentioned above can be obtained even by kneading to the extent that the filler is manually homogenized using a mortar, and thus the present invention has been completed.

Thus, in the curable composition for dentistry according to the embodiment of the present invention, it is necessary that the organic-inorganic composite filler (C) includes a curved surface-shaped organic-inorganic composite filler (C1) composed of organic-inorganic composite aggregate particles having a curved surface shape, and an irregular-shaped organic-inorganic composite filler (C2) composed of organic-inorganic composite aggregate particles having an irregular shape which includes an edge portion, and that a content ratio {C1/(C1+C2)} of the curved surface-shaped organic-inorganic composite filler (C1) accounting for the entire organic-inorganic composite filler (C) is 0.2 to 0.8 expressed in terms of a ratio of the total number of the curved surface-shaped organic-inorganic composite aggregate particles having a particle size of 5 μm or more, which constitute the curved surface-shaped organic-inorganic composite filler (C1), accounting for the total number of the organic-inorganic composite aggregate particles having a particle size of 5 μm or more. When the content ratio is below the lower limit value, the dryness occurs when the paste is stored over a long period of time. When the content rate exceeds the upper limit value, the paste has large stickiness and the shape retention deteriorates. The content ratio {C1/(C1+C2)} is preferably 0.3 to 0.7, and more preferably 0.3 to 0.6, from the viewpoint of the effect.

As can be seen from the above description, the curved surface-shaped organic-inorganic composite filler (C1) corresponds to the porous organic-inorganic composite filler obtained by the method mentioned in Patent Document 3, and the irregular-shaped organic-inorganic composite filler (C2) corresponds to those in which the porous organic-inorganic composite filler obtained by the method mentioned in Patent Document 3 is pulverized. For example, the irregular-shaped organic-inorganic composite filler (C2) can be produced by pulverizing the curved surface-shaped organic-inorganic composite filler (C1) using a vibration ball mill, a bead mill, a jet mill or the like.

When the porous organic-inorganic composite filler obtained by the method mentioned in Patent Document 3 is pulverized by a kneading operation during preparation of a curable composition for dentistry to form an irregular-shaped organic-inorganic composite filler (C2), the formation rate can be controlled by the kneading conditions. For example, the relationship between the kneading conditions and the formation rate is investigated in advance, and actual kneading is performed by employing the conditions which afford the formation rate which achieves a predetermined content ratio {C1/(C1+C2)} based on the relationship, thus making it possible to prepare a curable composition for dentistry with the above predetermined content. It is also possible to control the content ratio by using the change in viscosity or hardness of the paste during preparation of the curable composition for dentistry as an index. Usually, when only the curved surface-shaped organic-inorganic composite filler (C1) is used as the raw material, and a mechanical driven-type kneader such as a planetary mixer is used, a part of the curved surface-shaped organic-inorganic composite filler (C1) is pulverized into an irregular shape by the kneading operation, and the viscosity and hardness of the paste increase according to the kneading time. However, all of the curved surface-shaped organic-inorganic composite filler (C1) is not pulverized, and after reaching saturation, the change in viscosity and hardness of the paste is not observed when the kneading time exceeds a certain period of time. Therefore, the above kneading is performed using a little bit of the polymerizable monomer (A), and the end point is the time when the rate of change in viscosity or hardness of the paste becomes less than 10%, and then the remaining polymerizable monomer (A) is added and the viscosity and hardness of the paste are adjusted to an appropriate level, thus making it possible to prepare curable composition for dentistry with the above predetermined content. Meanwhile, when a mixed filler obtained by mixing the curved surface-shaped organic-inorganic composite filler (C1) and the irregular-shaped organic-inorganic composite filler (C2) in a specific ratio is used as the raw material, by employing, as the kneading method and kneading conditions, a method and conditions which enables prevention or ignorance of pulverization of the curved surface-shaped organic-inorganic composite filler (C1), the content ratio {C1/(C1+C2)} in the mixed filler substantially becomes the content ratio in the curable composition for dentistry.

The average particle size (grain size) of the organic-inorganic composite filler (C) may be 10 to 100 µm, and preferably 10 to 70 µm. When the average particle size of the organic-inorganic composite filler (C) is too small, the filler filling rate in the curable composition for dentistry decreases, thus causing a reduction in mechanical strength and deterioration of the operability due to stickiness. When the average particle size of the organic-inorganic composite filler (C) is too large, the dryness of the paste occurs, thus causing deterioration of the operability. The average particle size is a median diameter obtained based on the grain size distribution by the laser diffraction-scattering method. Specifically, the measurement is made on a sample prepared uniformly by dispersing 0.1 g of an organic-inorganic composite filler in 10 mL of ethanol.

The average particle size (grain size) is an average particle size of the organic-inorganic composite filler (C), and depends on the average particle size of the curved surface-shaped organic-inorganic composite filler (C1) and the average particle size of the irregular-shaped organic-inorganic composite filler (C2), and the mixing ratio of these fillers. Since the irregular-shaped organic-inorganic composite filler (C2) is also a pulverized product of the curved surface-shaped organic-inorganic composite filler (C1), its average particle size is smaller than the average particle size of the curved surface-shaped organic-inorganic composite filler (C1) before pulverization, and is usually about half of that of the curved surface-shaped organic-inorganic composite filler. Therefore, when only the curved surface-shaped organic-inorganic composite filler (C1) is used as the raw material, if those having the average particle size of larger than the above range (for example, 20 to 150 µm) are used, the average particle size after kneading can be adjusted within the above range. In the case of kneading under kneading conditions that pulverization during kneading hardly occurs, using a mixed filler in which a curved surface-shaped organic-inorganic composite filler (C1) and an irregular-shaped organic-inorganic composite filler (C2) are mixed in a specific ratio, a curved surface-shaped organic-inorganic composite filler (C1) and an irregular-shaped organic-inorganic composite filler (C2) each having a particle size such that the entire average particle size falls within the above range according to a pre-determined content ratio may be used.

It is possible to confirm the shape of the organic-inorganic composite aggregate particles constituting the curved surface-shaped organic-inorganic composite filler (C1) and the shape of the organic-inorganic composite aggregate particles constituting the irregular-shaped organic-inorganic composite filler (C2) by electron microscopic observation.

It is also possible to determine the content ratio {C1/(C1+C2)} by counting the number of the organic-inorganic composite aggregate particles having a particle size of 5 µm or more while classifying their shapes with electron microscopic observation of the inorganic filler (B) and the organic-inorganic composite filler (C) taken out from the curable composition for dentistry (for example, through steps such as filtration, solvent washing and drying), or electron microscopic observation of the surface (or cross section) of the cured body of the curable composition for dentistry. The particle size of the organic-inorganic composite aggregate particles for determining the content ratio {C1/(C1+C2)} was set at 5 µm or more for the reason that the shape can be easily determined by electron microscopic observation, and that the amount of the organic-inorganic composite aggregate particles having less than 5 µm is small, thus exerting very small influence on the true content and effect (when all particles can be counted).

The curved surface-shaped organic-inorganic composite filler (C1) is not particularly different from the porous organic-inorganic composite filler mentioned in Patent Document 3, except for the measurement method of the pore volume and the above-mentioned points, and the production method thereof is not particularly different from the method mentioned in Patent Document 3.

It is possible to use, as the inorganic primary particles, those composed of inorganic oxides such as amorphous silica, silica-zirconia, silica-titania, silica-titania-barium oxide, silica-titania-zirconia, quartz, alumina, titania, zirconia and glass. Of these, preferred are silica-based composite oxide particles, and particularly silica-zirconia particles. Spherical or substantially spherical inorganic primary particles having average uniformity of 0.6 or more are preferably used since they have excellent abrasion resistance and surface smoothness, and the organic-inorganic composite filler includes uniform pores, and openings thereof are closed with an organic resin phase, thus making it difficult for air bubbles to be included. The average particle size of the inorganic primary particles may be 10 to 1000 nm, preferably 40 to 800 nm, and more preferably 50 to 600 nm.

Such inorganic primary particles are surface-treated with a silane coupling agent as necessary and then spray-dried to obtain inorganic aggregate particles, which are immersed in a polymerizable monomer solution prepared by dissolving a polymerizable monomer and a polymerization initiator in an organic solvent, followed by removal of the organic solvent and further polymerization-curing, thus making it possible to obtain an organic-inorganic composite filler composed of organic-inorganic composite aggregate particles having an aggregated structure so that inorganic primary particles are bonded together through a resin layer covering at least part of the surface of the inorganic primary particles to form a void, in which the total pore volume of pores having a pore size measured by the nitrogen adsorption method in the range of 1 to 500 nm is 0.01 to 0.30 cm$^3$/g, and an average particle size is 10 to 100 µm.

As the polymerizable monomer, those which are the same as the above-mentioned polymerizable monomer (A) can be used. As the polymerization initiator, those which are the same as the below-mentioned polymerization initiator (D) can be used. As the organic solvent, methanol, ethanol, acetone, dichloromethane and the like can be preferably used. The content of the polymerizable monomer in the above polymerizable monomer solution is preferably 10 to 50 parts by mass based on 100 parts by mass of the organic solvent. The polymerizable monomer solution may be mixed with an ultraviolet absorber, a pigment, a dye, a polymerization inhibitor or the like.

Immersion of the inorganic aggregate particles in the polymerizable monomer solution is performed by mixing the inorganic aggregate particles in the polymerizable monomer solution so that the amount of the polymerizable monomer is set at 30 to 500 parts by mass, and particularly 50 to 200 parts by mass, based on 100 parts by mass of inorganic aggregate particles. After mixing, the mixture is preferably left to stand for 1 hour or more.

In this way, inorganic aggregate particles are immersed in a polymerizable monomer solution to fill aggregation gaps of the inorganic aggregate particles with the solution, followed by removal of the organic solvent and further polymerization-curing, thus making it possible to obtain a curved surface-shaped organic-inorganic composite filler (C1). It is preferable that the removal of the organic solvent is performed until the substantially total amount (usually 95% by mass or more) of the organic solvent is removed to obtain a visually smooth powder. The operation for removal of the organic solvent is not particularly limited as long as it is a method capable of performing such removal, and the operation can be preferably performed by reduced pressure drying (or vacuum drying) in which drying is performed under reduced pressure of, for example, 0.01 to 50 hPa, and particularly 0.1 to 10 hPa. The polymerization-curing may be performed by appropriately selecting a preferable method according to the type of the polymerization initiator used.

The curved surface-shaped organic-inorganic composite filler (C1) thus obtained is separately pulverized by the method as mentioned above, or pulverized during kneading using this as the raw material, thus making it possible to obtain an irregular-shaped organic-inorganic composite filler (C2).

<Polymerization Initiator (D)>

The polymerization initiator (D) is not particularly limited as long as it has a function of polymerizing the polymerizable monomer (A). However, it is preferable to use a photopolymerization initiator or a chemical polymerization initiator used in dental direct-filling restoration applications where curing is often performed in the oral cavity, and it is more preferable to use a photopolymerization initiator in that a mixing operation is not required and it is simple.

It is possible to use, as the chemical polymerization initiator, a known chemical polymerization initiator which is composed of two or more components and generate polymerization initiator species (radicals) when these components are brought into contact with each without limitation. Examples of the chemical polymerization initiator include those composed of various combinations such as organic peroxide/amines, organic peroxide/amines/organic sulfinic acids, organic peroxide/amines/aryl borates, aryl borates/acidic compound, and barbituric acid derivatives/copper compound/halogen compound. Of these, those made of organic peroxides/amines are preferable because they are easy to handle.

Examples of the organic peroxide include known hydroperoxides, peroxyketals, ketone peroxides, alkylsilyl peroxides, diacyl peroxides, peroxy esters and the like.

It is a preferred aspect that a chemical polymerization initiator composed of an organic peroxide and amines is further mixed with sulfinic acids such as benzenesulfinic acid, p-toluenesulfinic acid and a salt thereof; and barbituric acids such as 5-butylbarbituric acid.

Examples of the photopolymerization initiator include benzoinalkyl ethers, benzyl ketals, benzophenones, α-diketones, thioxanthone compounds, bisacylphosphine oxides and the like. To these photopolymerization initiators, reducing agents such as tertiary amines, aldehydes and sulfur-containing compounds may be added. These photopolymerization initiators may be mixed with photoacid generators such as diaryliodonium salt-based compounds, sulfonium salt-based compounds, sulfonic acid ester compounds, halomethyl-substituted-S-triazine derivatives and pyridinium salt-based compounds.

These polymerization initiators are sometimes used alone, and two or more thereof may be used after being mixed.

<Other Additives>

The curable composition for dentistry according to the embodiment of the present invention contains, in addition to the above-mentioned components (A) to (D), other additives as long as the effect thereof is not impaired. Specific examples thereof include a polymerization inhibitor, an ultraviolet absorber and the like. For the purpose of adjusting the viscosity, it is possible to mix a filler having a particle size which is sufficiently smaller than the wavelength of light and does not easily affect the color tone and transparency.

<Composition and Method for Preparation of Curable Composition for Dentistry>

Each amount of components (A) to (D) mixed in the curable composition for dentistry according to the embodiment of the present invention is usually as follows: the amount of the inorganic filler (B) is 50 to 350 parts by mass, and preferably 100 to 300 parts by mass; the amount of organic-inorganic composite filler (C) is 50 to 350 parts by mass, and preferably 100 to 300 parts by mass; and the amount of the initiator (D) is 0.01 to 10 parts by mass, and preferably 0.1 to 5 parts by mass, based on 100 parts by mass of the polymerizable monomer (A). From the viewpoint that the curable composition for dentistry exhibits paste properties with satisfactory operability, the content of the inorganic filler (B) and that of the organic-inorganic composite filler (C) are preferably 100 to 300 parts by mass based on 100 parts by mass of the polymerizable monomer (A), and the total content of the inorganic filler (B) and the organic-inorganic composite filler (C) is preferably 250 to 550 parts by mass. The mixing ratio of the inorganic filler (B) and the organic-inorganic composite filler (C) may be appropriately determined from the above range in consideration of the viscosity of the curable composition for dentistry and the mechanical strength of the cured body.

The curable composition for dentistry according to the embodiment of the present invention can be prepared by weighing each predetermined amount of the components (A) to (D), followed by mixing. At this time, it is preferable to mix under the condition that the inorganic filler (B) is dispersed in the polymerizable monomer (A). In order to exert the effect of the present invention, it is necessary that the organic-inorganic composite filler (C) including aggregation gaps is composed of the curved surface-shaped organic-inorganic composite filler (C1) and the irregular-shaped organic-inorganic composite filler (C2), and an abundance ratio {C1/(C1+C2)} of both in the curable composition for dentistry is 0.2 to 0.8. It is possible to prepare the curable composition for dentistry by adjusting the mixing ratio of the curved surface-shaped organic-inorganic composite filler (C1) and the irregular-shaped organic-inorganic composite filler (C2) so as to satisfy this condition, or pulverizing the curved surface-shaped organic-inorganic composite filler (C1) in the paste.

The curable composition for dentistry according to the embodiment of the present invention is particularly preferably used as a dental filling restoration material typified by a photocurable composite resin as mentioned above, but is not limited thereto, and it can also be preferably used for other applications. Examples of its use include dental cement, restoration materials for abutment construction, and the like.

Examples

The present invention will be described in more detail below by way of Examples, but the present invention is not limited to these Examples.

The abbreviations of the compounds used in the following Examples and Comparative Examples are as follows.

(1) Abbreviations (Polymerizable Monomer)

3G: Triethylene glycol dimethacrylate

GMA: 2,2-Bis[(3-methacryloyloxy-2-hydroxypropyloxy)phenyl]propane

UDMA: 1,6-Bis(methacrylethyloxycarbonylamino)-2,2-4-trimethylhexane (Inorganic filler)

F-1: Spherical (average uniformity of 0.95) silica-zirconia in which an average particle size of primary particles is 200 nm produced by the sol-gel method F-2: Spherical (average uniformity of 0.95) silica-zirconia in which an average particle size of primary particles is 400 nm produced by the sol-gel method F-3: Spherical (average uniformity of 0.95) silica-zirconia in which an average particle size of primary particles is 700 nm produced by the sol-gel method F-4: Product obtained by a surface treatment of F-1 with γ-methacryloyloxypropyltrimethoxysilane F-5: Product obtained by a surface treatment of F-2 with γ-methacryloyloxypropyltrimethoxysilane F-6: Product obtained by a surface treatment of F-3 with γ-methacryloyloxypropyltrimethoxysilane (Polymerization Initiator)

AIBN: Azobisisobutyronitrile

CQ: Camphorquinone

DMBE: Ethyl N,N-dimethyl-p-benzoate (2) Method for Measurement of Average Particle Size and Average Uniformity of Inorganic Filler Using a scanning electron microscope ("XL-30S", manufactured by Philips N.V.), the photographs of the powder were taken at magnifications of 5,000 to 100,000 times. Using an image analysis software (trade name "IP-1000PC", manufactured by Asahi Kasei Engineering Corporation), the images thus taken were processed, and then the number of particles in a unit visual field of the photographs (30 or more) and the primary particle size (maximum size) were measured and the number-average particle size was calculated based on the measured values by the following equation.

$$\text{Average particle size:} X = \sqrt[3]{\frac{\sum_{i=1}^{n} X_i^3}{n}} \text{ (Average volume diameter)}$$

$n$:Number of particles observed $X_i$:Particle size (diameter) of i-th particle For the particles observed in the unit visual field, the number (n: 30 or more), the major axis (Li) which is the maximum size of the particles, and the minor axis (Bi) which is the size in the direction orthogonal to the major axis were determined, and then the average uniformity of the inorganic filler was calculated by the following equation.

$$\text{Average uniformity} = \frac{\sum_{i=1}^{n} Bi/Li}{n}$$

(3) Average Particle Size (Grain Size) of Organic-Inorganic Composite Filler

An organic-inorganic composite filler (0.1 g) was dispersed in 10 mL of ethanol, followed by irradiation with ultrasonic waves for 20 minutes. Using a grain size distribution meter ("LS230", manufactured by Beckman Coulter, Inc.) by the laser diffraction-light scattering method, the median diameter of the volume statistics was determined by applying an optical model (Fraunhofer).

(4) Method for Measurement of Pore Volume of Aggregation Gaps in Organic-Inorganic Composite Filler In a sample cell, 1.0 g of an organic-inorganic composite filler was placed and then a pretreatment was performed by vacuum evacuation at 120° C. for 3 hours using a pretreatment device ("VacuPrep 061", manufactured by Shimadzu Corporation). Thereafter, using nitrogen as an adsorption gas and liquid nitrogen as a refrigerant, the total pore volume having a pore size in the range of 1 to 500 nm was determined using a pore distribution analyzer by the gas adsorption method ("TriStar 113020", manufactured by Shimadzu Corporation).

(5) Method for Preparation of Curable Composition for Dentistry

A polymerization initiator was added to a polymerizable monomer mixed in a predetermined amount ratio under red light to dissolve the polymerization initiator. A predetermined amount of filler was added thereto, followed by stirring to mix well until a uniform paste-like mixture was obtained. Further, this mixture was subjected to vacuum defoaming to obtain a paste of a curable composition for dentistry with a predetermined composition.

(6) Method for Evaluation of Abundance Ratio {C1/(C1+C2)} of Curved Surface-Shaped Organic-Inorganic Composite Filler (C1) and Irregular-Shaped Organic-Inorganic Composite Filler (C2) in Curable Composition for Dentistry A mold made of a fluororesin, having a diameter of 7 mm and a thickness of 1 mm was filled with a curable composition for dentistry, followed by polymerization-curing in the presence of air. Thereafter, the cured body was taken out from the mold, and the unpolymerized portion of the surface layer was washed with ethanol. The photographs of the washed surface were taken using a scanning electron microscope, and 100 particles having a particle size of 5 μm or more observed in a unit visual field of the photographs were randomly selected, and then the abundance ratio of the curved surface-shaped organic-inorganic composite filler and the irregular-shaped organic-inorganic composite filler was calculated.

(7) Method for Evaluation of Operability of Paste

The paste properties of a curable composition for dentistry before curing were evaluated based on the following criteria from the viewpoint of the operability. That is, those with less stickiness were rated as "B", those with particularly less stickiness were rated as "A", and those which are difficult to operate due to strong stickiness were rated as "C". Further, those with less dryness were rated as "B", those with particularly less dryness were rated as "A", and those which are difficult to operate due to strong dryness were rated as "C". Evaluation was performed immediately after preparation of the curable composition for dentistry and after storage at 37° C. for 6 months.

(8) Method for Evaluating of Shape Retention of Paste

The shape retention of a paste of a curable composition for dentistry before curing was evaluated by the following method. First, an artificial resin tooth that reproduces Class I cavity (diameter of 4 mm, depth of 2 mm) of in the center of the lower right No. 6 occlusal surface was filled with a paste of a curable composition for dentistry to impart the occlusal surface shape to the filled paste. Thereafter, the artificial resin tooth filled with the curable composition for dentistry was left to stand in an incubator at 50° C. for 20 minutes, and it was evaluated whether or not the imparted shape was retained. Specifically, those in which slight change in imparted shape was confirmed were rated as "B", those in which no change in imparted shape was confirmed were rated as "A", and those in which the imparted shape could not be retained were rated as "C". Evaluation was performed immediately after preparation of the curable composition for dentistry and after storage at 37° C. for 6 months.

(9) Method for Measurement of Bending Strength

A mold made of stainless steel was filled with a paste of a curable composition for dentistry and the paste was irradiated with light using a visible light irradiator POWER LIGHT (manufactured by Tokuyama Corporation) adherently to polypropylene in a state where the polypropylene was pressure-welded to the mold, by changing the place from one surface three times for 30 seconds each time so that lights would hit the entirety. Next, light irradiation of three times for 30 seconds each time was performed through the opposite surface similarly adherently to the polypropylene to obtain a cured body. The cured body was trimmed into a rectangular prism shape having a size of 2 mm×2 mm×25 mm with a #1500 water-resistant polishing paper, and this test piece was mounted on a testing machine ("AUTO-GRAPH AG5000D", manufactured by Shimadzu Corporation), and then the three-point bending fracture strength was measured at a distance between two fulcrums of 20 mm and a cross-head speed of 1 mm/minute. The bending strength $\sigma_B$ was determined by the following equation, and the average value evaluated for five test pieces was defined as the bending strength. $\sigma_B$ is the bending strength (Pa), P is the load at the time of breaking the test piece (N), S is the distance between the fulcrums (m), W is the width of the test piece (m), and B is the thickness of the test piece (m), respectively.

$$\sigma_B = \frac{3PS}{2WB^2}$$

The organic-inorganic composite filler was prepared by Production Examples 1 to 7.

Production Examples 1 to 3

An inorganic filler was put into water, and a dispersion containing the inorganic filler dispersed therein was obtained using a circulation type pulverizer SC Mill. Then, γ-methacryloyloxypropyltrimethoxysilane and acetic acid were added to water, followed by stirring to obtain a uniform solution having a pH of 4. This solution was added to the inorganic particle dispersion, followed by mixing uniformly. Then, the dispersion was dried by the spray-drying method to obtain an inorganic powder. For spray drying, a spray dryer (Spray Dryer "NL-5", manufactured by OHKAWARA KAKOHKI CO., LTD.) that collides with atomizing air at the tip of a nozzle to form fine particles was used, the atomizing pressure was set at 0.08 MPa, and the temperature was set at 230° C. Thereafter, the spray-dried inorganic powder was vacuum-dried at 120° C. for 15 hours to obtain inorganic aggregate particles.

A polymerizable monomer solution was then prepared by mixing a polymerizable monomer mixed in a predetermined amount ratio with AIBN as a polymerization initiator and methanol as an organic solvent, and inorganic aggregate particles and the polymerizable monomer solution were mixed so that the ratio of the polymerizable monomer and the inorganic aggregate particles became a predetermined ratio. After confirming that the mixture exhibits slurry-like properties, the mixture was left to stand for 1 hour.

While stirring with a rotary evaporator, the mixture was dried under the conditions of the pressure reduction degree of 10 hPa and a heating condition of 40° C. (using a hot water bath) for 1 hour to remove the organic solvent. A smooth powder was obtained by removing the organic solvent.

While stirring with a rotary evaporator, the powder was heated under the conditions of the pressure reduction degree of 10 hPa and a heating condition of 100° C. (using an oil bath) for 1 hour, followed by polymerization-curing of the polymerizable monomer in the powder to obtain a curved surface-shaped organic-inorganic composite filler. Then, the average particle size and the pore volume of the organic-inorganic composite filler thus obtained were measured. The results are shown in Table 1.

Production Example 4

An inorganic filler was put into water to obtain a dispersion in which the inorganic filler was dispersed using a circulation type pulverizer SC Mill. Then, γ-methacryloyloxypropyltrimethoxysilane and acetic acid were added to water, followed by stirring to obtain a uniform solution having a pH of 4. This solution was added to the inorganic particle dispersion, followed by mixing uniformly. Then, the dispersion was dried by a spray-drying method to obtain an inorganic powder. For spray drying, a spray dryer (Spray Dryer "TSR-2W", manufactured by Sakamoto Giken CO., LTD.), which is equipped with a disk rotating at a high speed and forms fine particles by a centrifugal force, was used, and the rotational speed of the disk was set at 9,000 rpm and the drying temperature was set at 200° C. Then, the spray-dried inorganic powder was vacuum-dried at 120° C. for 15 hours to obtain inorganic aggregate particles.

The polymerizable monomer mixed in a predetermined amount ratio was mixed with AIBN as a polymerization initiator and methanol as an organic solvent to prepare a polymerizable monomer solution, and inorganic aggregate particles and the polymerizable monomer solution were mixed so that the ratio of the polymerizable monomer and the inorganic aggregate particles became a predetermined ratio. After confirming that the mixture exhibits slurry-like properties, the mixture was left to stand for 1 hour.

While stirring with a rotary evaporator, the mixture was dried under the conditions of the pressure reduction degree of 10 hPa and a heating condition of 40° C. (using a hot water bath) for 1 hour to remove the organic solvent. A smooth powder was obtained by removing the organic solvent.

While stirring with a rotary evaporator, the powder was heated under the conditions of the pressure reduction degree of 10 hPa and a heating condition of 100° C. (using an oil bath) for 1 hour, followed by polymerization-curing of the polymerizable monomer in the powder to obtain a curved surface-shaped organic-inorganic composite filler. Then, the average particle size and the pore volume of the organic-inorganic composite filler thus obtained were measured. The results are shown in Table 1.

Production Example 5

The curved surface-shaped organic-inorganic composite filler produced in Production Example 1 was pulverized by a vibrating ball mill (zirconia ball particle size: 5 mm) to obtain an irregular-shaped organic-inorganic composite filler. Then, the average particle size and the pore volume of the organic-inorganic composite filler thus obtained were measured. The results are shown in Table 1.

Production Example 6

The curved surface-shaped organic-inorganic composite filler produced in Production Example 4 was pulverized by a vibrating ball mill (zirconia ball particle size: 5 mm) to obtain an irregular-shaped organic-inorganic composite filler. Then, the average particle size and the pore volume of the organic-inorganic composite filler thus obtained were measured. The results are shown in Table 1.

Production Example 7

The same inorganic aggregate particles (10 g) as in Production Example 1, GMA (28 g) and 3G (12 g) as polymerizable monomers, and AIBN as a polymerization initiator were put into a mortar, followed by mixing to prepare a paste-like mixture. This paste-like mixture was defoamed under reduced pressure, followed by polymerization-curing at 100° C. for 30 minutes. The cured product was pulverized with a vibrating ball mill (zirconia ball particle size: 5 mm) to obtain an irregular-shaped organic-inorganic composite filler. Then, the average particle size and the pore volume of the organic-inorganic composite filler thus obtained were measured. The results are shown in Table 1.

TABLE 1

| | Raw material | | Organic-inorganic composite filler | | | | |
|---|---|---|---|---|---|---|---|
| No. | Inorganic filler F-1 (Parts by mass) | Polymerizable monomer (Parts by mass) | Classification | Abbreviations | Average particle size (μm) | Total pore volume (cm³/g) | Shape |
| 1 | 100 | GMA (16)/3G (7) | Porous (C1) | CF-1 | 20 | 0.09 | Curved surface shape |
| 2 | 100 | GMA (25)/3G (10) | | CF-2 | 20 | 0.02 | Curved surface shape |
| 3 | 100 | GMA (2.5)/3G (1.0) | | CF-3 | 20 | 0.25 | Curved surface shape |
| 4 | 100 | GMA (16)/3G (7) | | CF-4 | 50 | 0.09 | Curved surface shape |
| 5 | 100 | GMA (16)/3G (7) | Porous (C2) | CF-5 | 12 | 0.09 | Irregular shape |
| 6 | 100 | GMA (16)/3G (7) | | CF-6 | 25 | 0.09 | Irregular shape |
| 7 | 100 | GMA (28)/3G (12) | Non-porous | CF-7 | 30 | 0.00 | Irregular shape |

Example 1

CQ (0.20 part by mass) and DMBE (0.35 part by mass) were completely dissolved in a polymerizable monomer composed of GMA (60 parts by mass) and 3G (40 parts by mass), and an inorganic filler F-4 (200 parts by mass), the curved surface-shaped organic-inorganic composite filler (100 parts by mass) obtained in Production Example 1, and the irregular-shaped organic-inorganic composite filler (100 parts by mass) obtained in Production Example 5 were mixed, and each component was manually mixed using a mortar until it reaches uniform consistency, followed by kneading for 20 minutes and further defoaming to prepare a curable composition for dentistry. Each physical property of the obtained curable composition for dentistry were evaluated based on the above method. The results are shown in Table 3.

Examples 2 to 9, Comparative Examples 1 to 5

According to the composition (parts by mass) shown in Table 2, curable compositions for dentistry of Examples 2 to 9 and Comparative Examples 1 to 5 were prepared in the same manner as in Example 1. Then, each physical property was evaluated. The results are shown in Table 3.

Examples 10, 11

CQ (0.20 part by mass) and DMBE (0.35 part by mass) as polymerization initiator were completely dissolved in a polymerizable monomer composed of GMA (60 parts by mass) and 3G (40 parts by mass) to prepare a polymerizable monomer mixture. To this polymerizable monomer mixture (80 parts by mass), an inorganic filler (200 parts by mass) and a curved surface-shaped organic-inorganic composite filler (200 parts by mass) were added according to the composition shown in Table 2, followed by kneading at a stirring blade rotational speed of 7 to 10 rpm for 30 minutes using a planetary movement type stirrer Planetary Mixer (manufactured by INOUE MFG., INC.). Then, the viscosity of the paste was measured every 30 minutes, and when the change in paste viscosity became less than 10%, the polymerizable monomer mixture (20 parts by mass) was added, followed by mixed until a uniform paste-like mixture was obtained to prepare a curable composition for dentistry. Each physical property of the obtained curable composition for dentistry was evaluated based on the above method. The results are shown in Table 3.

TABLE 2

| | | (A) Polymerizable monomer (Parts by mass) | (B) Inorganic filler (Parts by mass) | (C) Organic-inorganic composite filler | | Content ratio* $C1/(C1 + C2)$ |
| --- | --- | --- | --- | --- | --- | --- |
| | No. | | | (C1) Curved surface shape | (C2) Irregular shape | |
| Example | 1 | GMA (60)/3G (40) | F-4 (200) | CF-1 (100) | CF-5 (100) | 0.4 |
| | 2 | the same above | F-4 (200) | CF-1 (150) | CF-5 (50) | 0.7 |
| | 3 | the same above | F-4 (200) | CF-1 (50) | CF-5 (150) | 0.2 |
| | 4 | 3G (30)/UDMA (70) | F-4 (200) | CF-1 (100) | CF-5 (100) | 0.4 |
| | 5 | GMA (60)/3G (40) | F-5 (200) | CF-1 (100) | CF-5 (100) | 0.4 |
| | 6 | the same above | F-6 (200) | CF-1 (100) | CF-5 (100) | 0.4 |
| | 7 | the same above | F-4 (200) | CF-2 (100) | CF-5 (100) | 0.5 |
| | 8 | the same above | F-4 (200) | CF-3 (100) | CF-5 (100) | 0.3 |
| | 9 | the same above | F-4 (200) | CF-4 (100) | CF-6 (100) | 0.5 |
| | 10 | the same above | F-4 (200) | CF-1 (200) | — | 0.7 |
| | 11 | the same above | F-4 (200) | CF-4 (200) | — | 0.7 |
| Comparative Example | 1 | the same above | F-4 (200) | CF-1 (200) | — | 0.9 |
| | 2 | 3G (30)/UDMA (70) | F-4 (200) | CF-1 (200) | — | 0.9 |
| | 3 | GMA (60)/3G (40) | F-4 (200) | — | CF-5 (200) | 0.1 |
| | 4 | the same above | — | CF-1 (200) | CF-6 (200) | 0.6 |
| | 5 | the same above | F-4 (200) | Non-porous organic-inorganic composite filler: CF-7 (200) | | |

*Value in paste (curable composition) after kneading

TABLE 3

| | | \multicolumn{6}{c}{Evaluation results} | |
| | | \multicolumn{6}{c}{Operability} | |
| | | Stickiness | | Dryness | | Shape retention | | |
| No. | | Immediately after preparation | After 6 months | Immediately after preparation | After 6 months | Immediately after preparation | After 6 months | Bending strength (MPa) |
|---|---|---|---|---|---|---|---|---|
| Example | 1 | A | A | A | A | A | A | 150 |
| | 2 | A | A | A | A | A | A | 152 |
| | 3 | A | A | A | A | A | A | 148 |
| | 4 | A | A | A | A | A | A | 155 |
| | 5 | A | A | A | A | A | A | 155 |
| | 6 | B | B | A | A | A | A | 160 |
| | 7 | A | A | A | A | A | A | 135 |
| | 8 | A | A | A | A | A | A | 155 |
| | 9 | A | A | A | B | A | A | 148 |
| | 10 | A | A | A | A | A | A | 151 |
| | 11 | A | A | A | A | A | A | 148 |
| Comparative Example | 1 | C | C | A | A | C | C | 140 |
| | 2 | C | C | B | B | C | C | 142 |
| | 3 | B | A | B | C | B | A | 145 |
| | 4 | A | A | C | C | B | B | 145 |
| | 5 | A | A | B | C | B | B | 90 |

As can be understood from the results of Examples 1 to 9, when the conditions specified in the present invention were satisfied, high bending strength was exhibited, stickiness and dryness were reduced, and satisfactory shape retention was exhibited. There was small change in operability and shape retention due to long-term storage.

As is understood from the results of Examples 10 and 11, even when the organic-inorganic composite filler to be mixed is composed of only those having a curved surface shape, the curved surface-shaped organic-inorganic composite filler was pulverized in the step of preparing the curable composition for dentistry to set the abundance ratio to less than 0.8, thus making it possible to obtain the desired effect.

Meanwhile, as is understood from the results of Comparative Examples 1 and 2, when the organic-inorganic composite filler to be mixed was composed of only those having a curved surface shape, the paste exhibited large stickiness and low ability to retain the imparted shape.

As is understood from the results of Comparative Examples 3 and 5, when the organic-inorganic composite filler to be mixed is composed of only those having an irregular shape, the paste exhibited large dryness due to long-term storage. As is understood from the results of Comparative Example 5, when the organic-inorganic composite filler including no pores was mixed, the bending strength of the cured product of the curable composition for dentistry was significantly reduced.

As is understood from the results of Comparative Example 4, when an inorganic filler was not mixed, the paste exhibited large dryness.

The invention claimed is:

1. A curable composition for dentistry, comprising
a polymerizable monomer (A);
an inorganic filler (B) having an average particle size of 0.1 to 1 μm;
an organic-inorganic composite filler (C), and
a polymerization initiator (D),
the organic-inorganic composite filler (C) comprising organic-inorganic composite aggregate particles having an aggregated structure where inorganic primary particles having an average particle size of 10 to 1,000 nm are bonded together through a resin layer covering at least part of the surface of the inorganic primary particles so as to form a void;
the organic-inorganic composite filler (C) having pores where a total pore volume of pores having a pore size measured by a nitrogen adsorption method in the range of 1 to 500 nm is 0.01 to 0.30 cm$^3$/g;
the organic-inorganic composite filler (C) having an average particle size of 10 to 100 μm;
wherein the organic-inorganic composite filler (C) comprises a curved surface-shaped organic-inorganic composite filler (C1) composed of organic-inorganic composite aggregate particles having a curved surface shape, and an irregular-shaped organic-inorganic composite filler (C2) composed of organic-inorganic composite aggregate particles having an irregular shape which comprises an edge portion, and
wherein a content ratio {C1/(C1+C2)} of the curved surface-shaped organic-inorganic composite filler (C1) accounting for the entire organic-inorganic composite filler (C) is 0.2 to 0.8, the content ratio being expressed in terms of a ratio of the total number of the curved surface-shaped organic-inorganic composite aggregate particles which have a particle size of 5 μm or more and which constitute the curved surface-shaped organic-inorganic composite filler (C1), accounting for the total number of the organic-inorganic composite aggregate particles having a particle size of 5 μm or more.

2. The curable composition for dentistry according to claim 1, wherein the organic-inorganic composite filler (C) is an organic-inorganic composite filler obtained by spray-drying inorganic primary particles to form aggregate particles, and impregnating pores of the aggregate particles with a polymerizable monomer component, followed by polymerization.

3. The curable composition for dentistry according to claim 1, wherein the irregular-shaped organic-inorganic composite filler (C2) is composed of a pulverized product of the curved surface-shaped organic-inorganic composite filler (C1).

4. The curable composition for dentistry according to claim 1, wherein the contents of the inorganic filler (B) and the organic-inorganic composite filler (C) are 100 to 300 parts by mass based on 100 parts by mass of the polymerizable monomer (A), respectively, and the total content of the inorganic filler (B) and the organic-inorganic composite filler (C) is 250 to 550 parts by mass based on 100 parts by mass of the polymerizable monomer (A).

5. The curable composition for dentistry according to claim 1, wherein both the shape of the inorganic particles constituting the inorganic filler (B) and the shape of the inorganic primary particles in the organic-inorganic composite aggregate particles constituting the organic-inorganic composite filler (C) are spherical or substantially spherical.

\* \* \* \* \*